United States Patent [19]
Yafai

[11] 4,304,246
[45] Dec. 8, 1981

[54] DENTAL FLOSS HOLDER

[76] Inventor: Zaid A. Yafai, 66 Boerum Pl., Apt. 3-c,, Brooklyn, N.Y. 11201

[21] Appl. No.: 136,530

[22] Filed: Apr. 2, 1980

[51] Int. Cl.³ .................................... A61C 15/00
[52] U.S. Cl. .................................................. 132/91
[58] Field of Search ............................. 132/90, 91

[56] References Cited
U.S. PATENT DOCUMENTS

| | | | |
|---|---|---|---|
| 2,162,240 | 6/1939 | Boldusoff | 132/91 |
| 2,180,522 | 11/1939 | Henne | 132/91 |
| 2,463,660 | 3/1949 | Turenchalk et al. | 132/91 |
| 2,612,176 | 9/1952 | Sam | 132/91 |
| 2,650,598 | 9/1953 | Rodosci | 132/91 |
| 2,981,264 | 4/1961 | DeFelice | 132/91 |

Primary Examiner—G. E. McNeill
Attorney, Agent, or Firm—Richard L. Miller

[57] ABSTRACT

An implement for holding dental floss in an operative position, in order to clean the crevices between the teeth; the implement including a U-shaped frame of flexible material, and a dental floss made into an endless loop, and which rests in a longitudinal groove around the outer side of the frame, and which also bridges across the space between the frame ends so that the floss across the space is adaptable for use between the teeth.

1 Claim, 6 Drawing Figures

U.S. Patent  Dec. 8, 1981  4,304,246
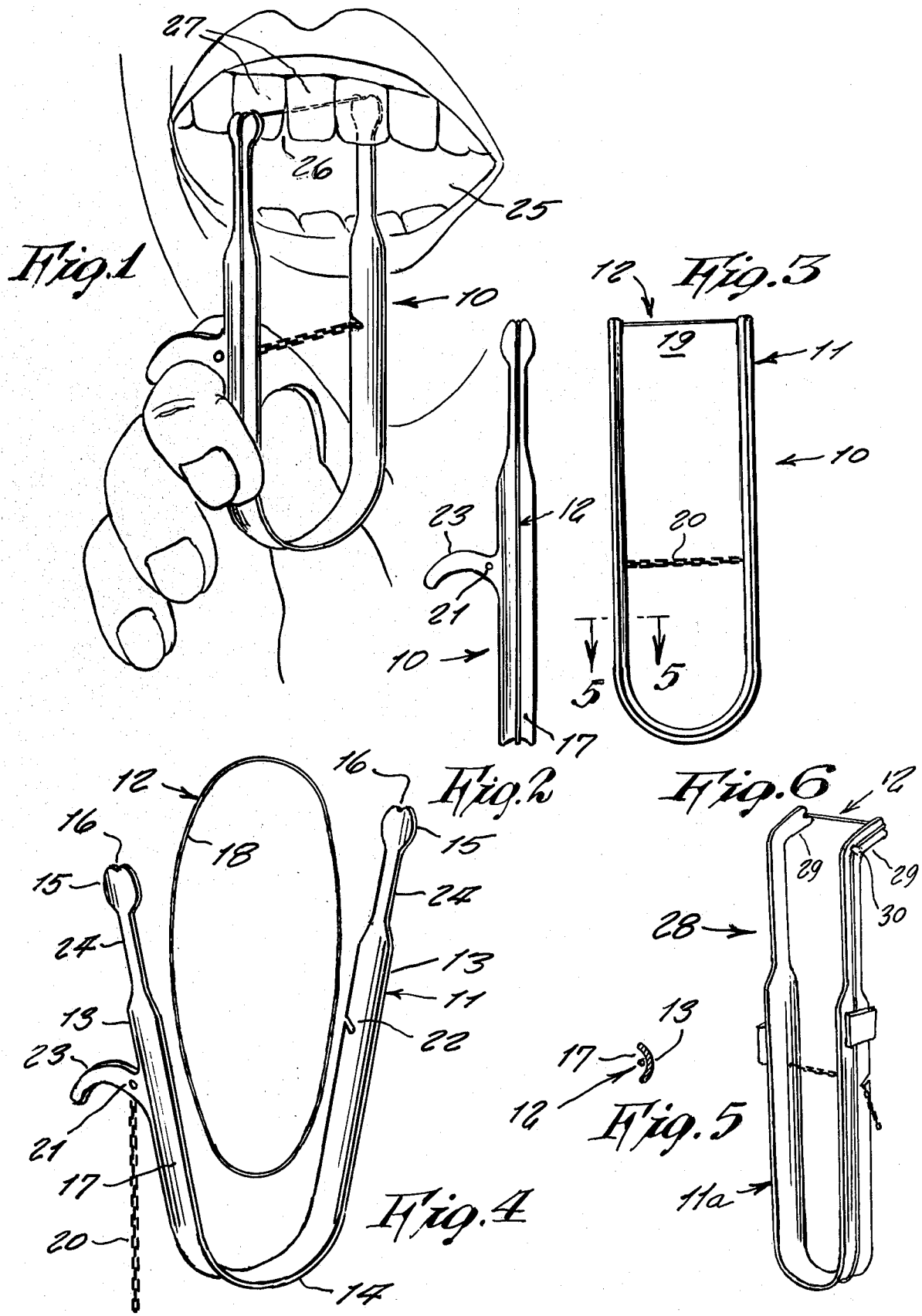

DENTAL FLOSS HOLDER

BACKGROUND OF THE INVENTION

This invention relates generally to hygienic equipment. More specifically it relates to dental care equipment.

The use of dental floss for removal of food particles from between the teeth, so as to prevent tooth decay, is well known. However the method of its application can be uncomfortable because in order to maintain the floss taut, it must be grasped between two fingers at each of two spaced-apart places, and then two of these fingers must get into the person's mouth so as to pass the floss into the crevices between the teeth. This situation is therefore in need of an improvement.

SUMMARY OF THE INVENTION

Accordingly it is a principal object of the present invention to provide a dental floss holder which maintains the floss taut on a small frame, and one end of the frame thus is entered in the mouth and behind the teeth, so that it is more comfortable than placing two fingers inside the mouth.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

The Figures on the drawings are briefly described as follows:

FIG. 1 is a perspective view of the invention shown in operative use.

FIG. 2 is a side view thereof.

FIG. 3 is a plan view.

FIG. 4 is a perspective view of the invention frame and dental floss shown disassembled.

FIG. 5 is a transverse cross sectional view on line 5—5 of FIG. 3.

FIG. 6 is a perspective view of another design of the holder having bent over ends so as to still more easily reach in a mouth.

DETAILED DESCRIPTION OF PREFERRED EMBODIMENT

Referring now to the drawing in greater detail, and more particularly to FIGS. 1 through 5 thereof, at this time, the reference numeral 10 represents a dental floss holder according to the present invention, wherein there is a frame 11 and a dental floss 12 that is supported upon the frame.

The frame is a generally U-shaped member made either from a molded plastic or stamped from a sheet metal; and which is resilient so that the fork legs 13 thereof can be flexed toward each other from the position shown in FIG. 4 to the position shown in FIG. 2. Thus if made from metal, it should be a spring steel so to normally urge the legs to spread apart. A bendable, semi-circular portion 14 is between one ends of the legs.

A terminal, opposite end 15 of each leg includes a shallow notch 16 across its center and which aligns with a center of a shallow trough 17 extending longitudinally all around the outer side of the frame, and which forms a channel inside of which the dental floss 12 is retained.

The dental floss is comprised of a conventional polyester dental floss thread that is flexible, smooth, thin and very strong so that it resists breaking. However while conventional dental floss is retailed as a long thread wound up on some form of spool, the dental floss of the present invention is made into an endless band or loop 18, so that it can snap around the frame, seating in the trough 17, and notches 16, and extending across the gap or space 19 between the terminal ends of the two legs.

The resilience of the frame serves to maintain the floss taut as it extends across the gap. However this tension can be selectively controlled by means of a chain 20 anchored at one end in a hold 21 and the opposite end being adjustably fitted in a notch 22 along one leg; the hole 21 being located in a base of a finger rest 23 formed integrally along one side edge of the other leg.

It is to be noted that a portion 24 of each leg located near a terminal end thereof, is made narrowed so as to more comfortably fit into a person's mouth 25.

In operative use, the floss portion between the notches 16 is inserted into the crevice 26 between teeth 27 in order to clean out the same, as shown in FIG. 1.

A modified design of dental floss holder 28, shown in FIG. 6, is a same as dental floss holder 10, except that a terminal end of each leg includes a sideward offset 29 so that the axis of the floss portion between notches 16 does not intercept the longitudinal axis of the legs, and thus is more accessible for easier reach into all crevices. A spur 30 molded or punched out on each leg holds the floss inside the trough where the trough angles at the base of the offset. The frame 11a, here shown, does not include the finger rests.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

I claim:

1. A dental floss holder, comprising in combination, a U-shaped frame, and a dental floss snap fitted around said frame, said frame including a pair of fork-like legs and a generally semi-circular portion between one end of said legs, a gap between an opposite terminal ends of said legs, and said dental floss extending across said gap; said frame being of resilient material so that said legs are squeezable toward each other; said dental floss comprising a polyester thread made into an endless band for extending around said frame and across said gap; and a chain secured at one end to a longitudinally intermediate portion of one said leg while an opposite end portion of said chain is adjustably fitted in a notch along a longitudinally intermediate portion of the other of said legs for adjusting a tension of said dental floss.

* * * * *